United States Patent
Pan et al.

(10) Patent No.: US 12,258,604 B2
(45) Date of Patent: Mar. 25, 2025

(54) METHOD FOR PROMOTING ANAEROBIC DIGESTION USING CARBONYL IRON

(71) Applicants: Institute of Agricultural Resources and Regional Planning, Chinese Academy of Agricultural Sciences, Beijing (CN); Junyi Ma, Beijing (CN); Junting Pan, Beijing (CN)

(72) Inventors: Junting Pan, Beijing (CN); Junyi Ma, Beijing (CN)

(73) Assignee: Institute of Agricultural Resources and Regional Planning, Chinese Academy of Agricultural Sciences, Beijing (CN)

( * ) Notice: Subject to any disclaimer, the term of this patent is extended or adjusted under 35 U.S.C. 154(b) by 0 days.

(21) Appl. No.: 18/889,673

(22) Filed: Sep. 19, 2024

(65) Prior Publication Data
US 2025/0011820 A1    Jan. 9, 2025

Related U.S. Application Data

(63) Continuation of application No. PCT/CN2022/087597, filed on Apr. 19, 2022.

(30) Foreign Application Priority Data

Apr. 15, 2022    (CN) .......................... 202210398688.8

(51) Int. Cl.
*C12P 5/02*    (2006.01)
*B09B 3/65*    (2022.01)
(Continued)

(52) U.S. Cl.
CPC ............... *C12P 5/023* (2013.01); *B09B 3/65* (2022.01); *C02F 3/28* (2013.01); *B09B 2101/70* (2022.01)

(58) Field of Classification Search
CPC ...... C02F 9/00; C02F 1/20; C02F 1/74; C02F 3/28; C02F 3/341; C02F 11/04;
(Continued)

(56) References Cited

U.S. PATENT DOCUMENTS

2016/0376205 A1*  12/2016  Lyu ......................... C10G 1/00
                                                                 71/10
2022/0064043 A1    3/2022  Dai et al.

FOREIGN PATENT DOCUMENTS

CN    107522375 A    12/2017
CN    109207527 A    1/2019
(Continued)

OTHER PUBLICATIONS

Machine-generated English translation of CN 113087332, generated on Nov. 12, 2024.*
(Continued)

*Primary Examiner* — Fred Prince
(74) *Attorney, Agent, or Firm* — Pilloff Passino & Cosenza LLP; Rachel Pilloff; Sean Passino

(57) ABSTRACT

Disclosed is a method for promoting anaerobic digestion using carbonyl iron, relating to the technical field of biological fermentation. The method includes the following steps: adding carbonyl iron into a fermentation broth for anaerobic digestion. According to the present disclosure, a substrate added in the fermentation broth is animal manure, kitchen waste or tail vegetables.

3 Claims, 4 Drawing Sheets

(51) Int. Cl.
*C02F 3/28* (2023.01)
*B09B 101/70* (2022.01)

(58) Field of Classification Search
CPC ..... C02F 11/125; C02F 11/126; C02F 11/145; C02F 11/18; C02F 2101/101; C02F 2101/105; C02F 2101/16; C02F 2103/20; C02F 2209/02; C02F 2209/06; C01B 25/26; C01B 25/265; C05F 3/00; C05F 17/15; C05F 17/40; C05F 17/50; C05F 17/10; Y02A 40/20; Y02E 50/30; Y02P 20/145; Y02W 30/40
USPC ................................................ 210/603, 631
See application file for complete search history.

(56) References Cited

FOREIGN PATENT DOCUMENTS

| CN | 112047590 A | 12/2020 | |
|---|---|---|---|
| CN | 112094012 A | 12/2020 | |
| CN | 113087332 A | 7/2021 | |
| CN | 113698039 A | 11/2021 | |
| CN | 114291989 A | 4/2022 | |
| KR | 20190063585 A | 6/2019 | |
| TW | 458818 B | * 10/2001 | .............. C02F 11/04 |

OTHER PUBLICATIONS

Machine-generated English translation of CN 113698039, generated on Nov. 12, 2024.*
Machine-generated English translation of TW 458818, generated on Nov. 12, 2024.*
Ma Junyi, "Mitigating transformation of ammonia and fatty acids during anaerobic digestion by biochar coupled iron nanoparticles," China's doctoral dissertation full-text database engineering technology I series No. 2. Date of issue: Feb. 15, 2022, Related pp. Section 4.1.2, 4.3, 5.3 and 6.3. Claims involved: 4-6 (abstract translated).
Pan Jun-Ting et al., "The performance of biochar-mediated anaerobic digestion of chicken manure," China Environmental Science, Date of issue: 20161231, Related p. pp. 2716-2721, vol. 36, No. 9. Claims involved: 1-6 (abstract translated).
International Search Report issued in corresponding PCT Application No. PCT/CN2022/087597, dated Dec. 16, 2022.
First Office Action for China Application No. 202210398688.8, mailed Sep. 16, 2022.
Notification to Grant Patent for China Application No. 202210398688.8, mailed Nov. 21, 2022.
First Search Report for China Application No. 202210398688.8, dated Sep. 9, 2022.
Supplementary Search Report for China Application No. 202210398688.8, dated Nov. 9, 2022.

* cited by examiner

METHOD FOR PROMOTING ANAEROBIC DIGESTION USING CARBONYL IRON

CROSS-REFERENCE TO RELATED APPLICATIONS

This application is a continuation of PCT/CN2022/087597, filed Apr. 19, 2022 and claims priority of Chinese Patent Application No. 202210398688.8, filed on Apr. 15, 2022, the entire contents of which are incorporated herein by reference.

TECHNICAL FIELD

The present disclosure relates to the technical field of biological fermentation, and in particular to a method for promoting anaerobic digestion using carbonyl iron.

BACKGROUND

Various microorganisms are utilized in anaerobic digestion to obtain methane-rich clean energy and nutrient-rich biogas that may be used as fertilizers while treating agricultural wastes; in this process, the energy and organic matter consumed for production and domestic use are supplemented and balanced. Nevertheless, there may be a mismatch between the physical and chemical properties of materials and the metabolic demands of microorganisms, which leads to the accumulation of intermediate metabolites and the inhibition of microbial activities, thus causing the digestive system to be inefficient and unstable, and restricting the highly effective and resourceful utilization of agricultural wastes.

One of the materials most likely to cause inhibition in the anaerobic digestion of livestock and poultry manure is chicken manure, which, with high content of nitrogen and easy to rot, is prone to produce a large amount of fatty acids and ammonia nitrogen in the anaerobic digestion process, and the neutralization of the two makes it difficult to diagnose and regulate the established inhibition by conventional means, such as pH value, and the phenomenon where gas production stagnates, but pH value is in the normal range is often found in the anaerobic digestion project using chicken manure as the substrate. Accordingly, the metabolism of anaerobic digestion microbial population is required to be balanced, the process of anaerobic digestion is to be optimized with higher efficiency and stability, thereby ensuring the highly efficient anaerobic treatment of chicken manure.

SUMMARY

The objective of the present disclosure is to provide a method for promoting anaerobic digestion using carbonyl iron, so as to solve the problems existing in the prior art. According to the present disclosure, the anaerobic digestion performance is improved by applying biochar-coupled carbonyl iron to anaerobic digestion, which in turn improves methane production.

In order to achieve the above objectives, the present disclosure provides the following technical schemes:

The present disclosure provides a method for promoting anaerobic digestion using carbonyl iron, including the following steps: adding carbonyl iron into a fermentation broth for anaerobic digestion.

Optionally, an addition amount of the carbonyl iron is 6 weight percent (wt %) of volatile solids of a substrate added in the fermentation broth.

Optionally, the substrate is animal manure, kitchen waste or tail vegetables.

Optionally, the fermentation broth is also added with biochar.

Optionally, an addition amount of the biochar is 2 wt % of the volatile solids of the substrate added in the fermentation broth.

Optionally, the substrate is animal manure, kitchen waste or tail vegetables.

As an important component of cellular enzymes, iron is also an essential trace element for the growth and metabolism of anaerobic microorganisms, with essential importance for the biosynthesis of methane. It is a relatively active metal widely distributed in nature, possessing good electrical conductivity and strong ferromagnetism. In the existing technology, elemental iron is applied in the anaerobic digestion system mainly in the form of monolithic iron such as nano-iron, where the reduction properties of zero-valent iron are mainly utilized to maintain a low redox potential, and the electron transfer process between syntrophic fatty acid oxidizing bacteria and hydrogen-consuming methanogens is facilitated by the excellent electrical conductivity of the iron to accelerate the degradation of the volatile fatty acids (VFAs). Carbonyl iron ($Fe(CO)_5$) powder is an iron powder of reduced elemental state, which is used in large quantities for iron nutritional fortification and iron supplementation medicines. Synthesized by using raw material of iron block and carbon monoxide under high temperature and high pressure, the carbonyl iron powder is a pentacarbonyl iron complex with an average particle size of 4.8 micrometers (m) and an onion globular structure, and has the characteristics of high purity, fine particle and high surface activity. Study has found that carbonyl iron powder has higher stability compared with zero-valent iron monomers, and that carbonyl iron is in the 0-valent state and has higher reactivity compared with magnetite. Carbonyl iron serves as a partial source of carbon and iron for microbial growth at the same time, and microbial uptake of iron from carbonyl iron is better than that of nano-iron; moreover, carbonyl iron shows higher bioaffinity than nano-iron, and anaerobic microorganisms tolerate carbonyl iron better than nano-iron, with a better affinity between carbonyl iron and anaerobic microorganisms. Furthermore, the special chemical structure and physicochemical properties of carbonyl iron also give it a good electron transfer efficiency. Therefore, the application of carbonyl iron in anaerobic digestion system has a greater potential for methane production enhancement in terms of micronutrient supplementation and promotion of electron transfer between microbial species.

The application of biochar in anaerobic digestion systems has been well developed, and through the mechanisms of removing inhibitors by adsorption, providing attachment space for microorganisms, and facilitating electron transfer between microbial species, biochar is better capable of increasing methane production. With good carbon skeleton and stability, biochar may facilitate the maintenance of iron reactivity and promote the effective state dispersion of iron when coupled with powdered iron materials for application in anaerobic digestion systems. Besides, a weak primary cell is formed within the digestive system by utilizing the potential difference that exists between iron and charcoal, thus forming a microelectrolytic system that promotes the degradation of organic matter and provides sufficient preconditioning substrate for methanogenic bacteria. Therefore, the coupled application of carbonyl iron and biochar to anaerobic digestion systems provides a great potential for methane production enhancement.

The present disclosure achieves the following technical effects.

The carbonyl iron promotes the microbial iron respiration and thus accelerates the degradation of complex organic matter on the one hand, and supplies the microorganisms with iron supplementation necessary for their growth on the other hand, showing promotional effects on both hydrolytic acidifying bacteria and methanogenic bacteria.

Under the coupled addition of biochar and carbonyl iron for anaerobic digestion, a synergistic effect is expected to further promote the production of inducible enzymes and the synthesis of intermediary metabolites required by microorganisms, thereby shortening the acclimatization period of the microorganisms. Due to the potential difference between iron and charcoal, biochar and carbonyl iron may form a microelectrolytic system within the anaerobic digestion system, acting as an anode and cathode, respectively, to donate and accept electrons, and synergistically facilitating electron transfer in the reciprocal methanogenesis pathway.

By adding biochar, the pH of the fermentation broth is lowered, while by adding carbonyl iron, the pH of the fermentation broth is increased, and a more significant enhancement of pH is achieved by the coupled addition of biochar and carbonyl iron.

Biochar and carbonyl iron regulate the soluble salt concentration by adjusting the conductivity of the fermentation broth, thereby increasing the activity of anaerobic digestive microorganisms.

Biochar and carbonyl iron may also be applied to anaerobic digestion of food waste and other substrates.

BRIEF DESCRIPTION OF THE DRAWINGS

In order to explain the embodiments of the present disclosure or the technical scheme in the prior art more clearly, the drawings needed in the embodiments will be briefly introduced below. Obviously, the drawings described below are only some embodiments of the present disclosure, and other drawings may be obtained according to these drawings without creative work for ordinary people in the field.

DETAILED DESCRIPTION OF THE EMBODIMENTS

Figure 1:
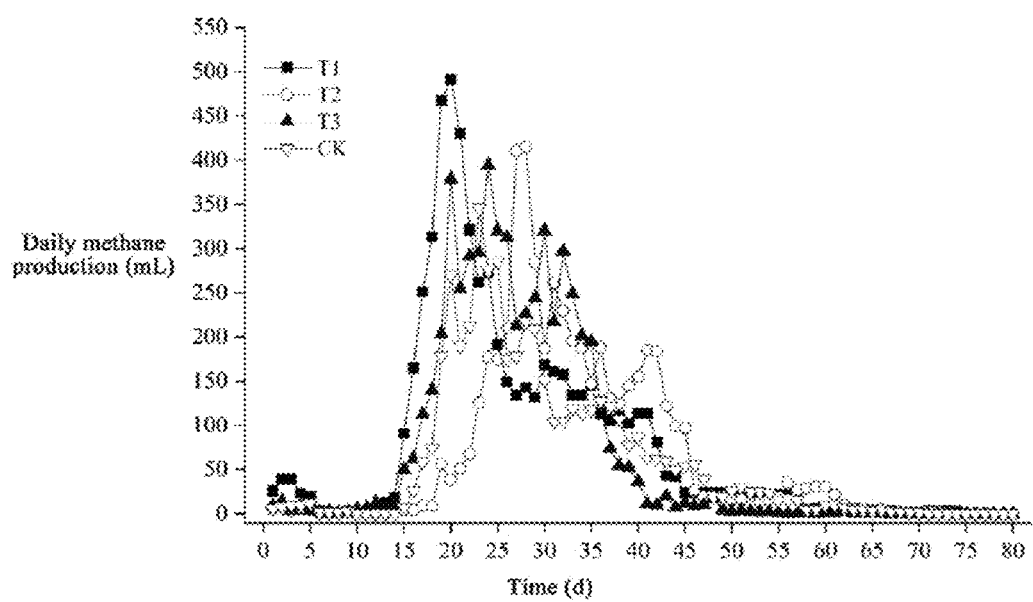
FIG. 1 illustrates the daily methane production in a process of anaerobic digestion.

A number of exemplary embodiments of the present disclosure will now be described in detail, and this detailed description should not be considered as a limitation of the present disclosure, but should be understood as a rather detailed description of certain aspects, characteristics and embodiments of the present disclosure.

It should be understood that the terminology described in the present disclosure is only for describing specific embodiments and is not used to limit the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges may be independently included or excluded from the range.

Unless otherwise specified, all technical and scientific terms used herein have the same meaning as commonly understood by one of ordinary skill in the art to which this disclosure relates. Although the present disclosure only describes the preferred methods and materials, any methods and materials similar or equivalent to those described herein can also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes can be made to the specific embodiments of the present disclosure without departing from the scope or spirit of the present disclosure. Other embodiments will be apparent to the skilled person from the description of the disclosure. The description and embodiments of the present disclosure are exemplary only.

The terms "including", "comprising", "having" and "containing" used in this specification are all open terms, which means including but not limited to.

The method of the present disclosure is applicable to perishable organic matter such as animal manure, kitchen waste, tail vegetables, and so on. The present disclosure illustrates a method for promoting anaerobic digestion using biochar coupled with carbonyl iron with chicken manure as a substrate.

Embodiment 1

1. Experimental Materials

The substrate used for anaerobic digestion is chicken manure collected from a large-scale farm, and the contents of total solids (TS) and volatile solids (VS) of the raw material are 24% and 15%, respectively. The inoculum is obtained from a continuous stirred anaerobic digestion reactor operating normally at medium temperature (36±1 degrees Celsius (° C.)) in a laboratory with 97% water content. The carbonyl iron powder is purchased from Beijing Ruidong Mianyuan Environmental Protection Technology Co., Ltd., with a particle size of 1-3 μm. The Biochar is prepared from waste fruit trees by pyrolysis, with a final temperature of 550° C., a residence duration of 2 hours, and the biochar is pulverized to a particle size of 0.3 to 0.45 millimeter (mm).

2. Experimental Methods

Volatile solid mass of 10.362 grams (g) of chicken manure is added to each of the four 500 milliliters (mL) anaerobic sequencing batch reactors, followed by inoculation with 120 mL of inoculum, with tap water to finalize the volume to an effective volume of 400 mL of the reactors. The four 500 mL anaerobic sequencing batch reactors are labeled as T1, T2, T3, and CK respectively, where 2% biochar and 6% carbonyl iron powder relative to the mass of volatile solids of the chicken manure are added to T1, 2% biochar relative to the mass of volatile solids of the chicken manure is added to T2, 6% carbonyl iron powder relative to the mass of volatile solids of the chicken manure is added to T3, and CK is the control, in which no biochar and carbonyl iron powder are added.

The biogas produced by the fermentation flows from the outlet hole above the reactor through a silica gel tube into an aluminum foil gas bag for storage. The fermentation cycle is 80 days (d), with a daily measurement of gas production volume, gas composition analysis every 3 d, and sample collection of fermentation broth every 5 d. The fermentation broth is mixed well before sampling, and about 10 mL of samples are collected each time.

3. Experimental Results

Figure 2:
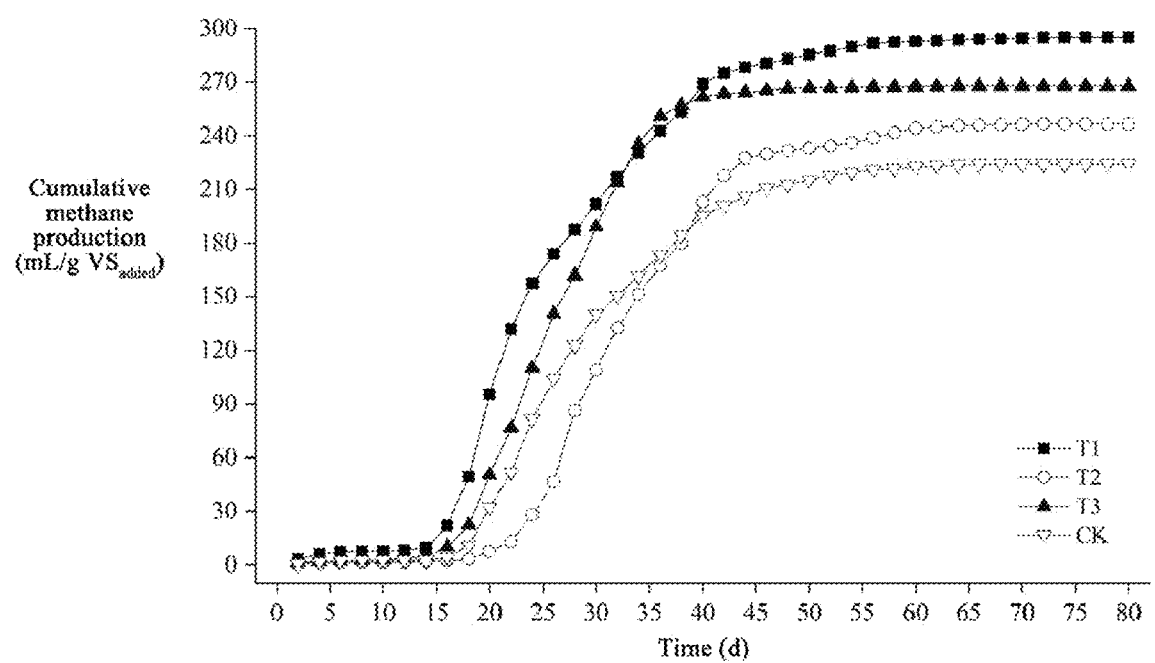
FIG. 2 shows the cumulative methane production in the process of the anaerobic digestion.

FIG. 1 and FIG. 2 show the daily and cumulative methane production during anaerobic digestion, respectively. In all treatments, a methane production stagnation period is observed and two daily methane production peaks are exhibited, following generally the same trend. The end product of anaerobic digestion is methane, and the metabolic activity of the microorganisms in the reactor as well as the efficiency of degradation of macromolecular organic matter within the fermentation substrate are represented by the yield of methane. hydrolysis reaction prevails in the reactor during the pre-fermentation period, and most of the methanogenic microorganisms are in growth stagnation, requiring metabolic adjustments for a period of time to adapt to the new growth environment, and the methane production at this stage is relatively low. In groups T1, T2, T3 and CK, the stagnation is continued for 12 d, 18 d, 14 d and 15 d, respectively, with the longest stagnation in the treatment with biochar alone and the shortest in the treatment with biochar coupled with carbonyl iron powder. It is possible that the biochar at this stage mainly acts to enrich hydrolytic acidifying bacteria and activates methanogenic bacteria weakly, resulting in high concentrations of intermediate metabolites. In contrast, carbonyl iron accelerates the degradation of complex organic matter by promoting microbial iron respiration on the one hand, and provides microorganisms with iron supplementation necessary for their growth on the other hand, promoting both hydrolytic acidifying bacteria and methanogenic bacteria. The biochar and carbonyl iron are coupled to provide a synergistic effect to further promote the production of inducible enzymes and the synthesis of intermediary metabolites required by microorganisms, and to shorten the acclimatization period of microorganisms.

The variation trend of daily methane production is more consistent with that of the typical growth curve of microorganisms, and after the stagnation period, the methanogenic microorganisms grow into the logarithmic period, with methane production rising linearly. Of all the treatments, group T1 shows the earliest appearance of daily methane production peak and the highest peak value, reaching 491 mL on the $20^{th}$ d; the peaks of T2, T3 and CK groups are on the $28^{th}$, $22^{nd}$ and $23^{rd}$ d, respectively, with the peak values of 415 mL, 445 mL and 345 mL, respectively, which indicating that the coupling of biochar with carbonyl iron advance the appearance of the methane production peak of anaerobic digestion and significantly increase the daily methane production peak (P<0.01).

In T1, T2, T3 and CK groups, the cumulative methane production is 295 mL/g volatile solids (VS), 246 mL/gVS, 268 mL/gVS and 224 mL/gVS, respectively, that is, by coupling or adding biochar and carbonyl iron alone, the cumulative methane production is significantly increased (p<0.05) by 31.5%, 9.9% and 19.4% respectively as compared with the control group. This may be attributed to the fact that carbonyl iron and biochar serve as conductive materials to participate in the direct interspecies electron transfer of mutualistic microorganisms, therefore the oxidative degradation of volatile fatty acids produced by acidification is accelerated and the production of $CH_4$ via the $CO_2$ hydrogenation pathway is facilitated. Moreover, a microelectrolytic system is likely to be formed within the anaerobic digestion system by biochar and carbonyl iron because of the potential difference between the iron and charcoal, acting as anode and cathode, respectively, to confer and accept electrons and synergistically facilitate electron transfer in the reciprocal methanogenesis pathway.

Figure 3:
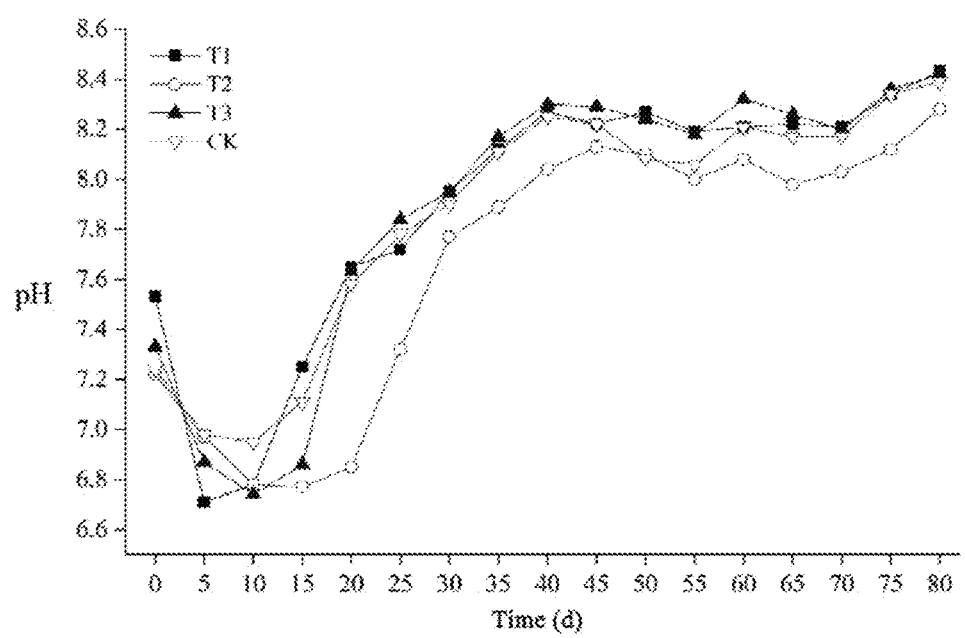
FIG. 3 shows the pH variation in the process of the anaerobic digestion.

FIG. 3 illustrates the pH changes during anaerobic digestion, and all treatments exhibit basically the same trend of change, with a downward and then an upward trend. The rapid decrease of pH in each treatment during the first 5 d of fermentation is attributed to the massive accumulation of organic acids in the system as a result of hydrolytic acidification of complex organic matter. Upon fermentation initiation, the pH values of the T2 and CK groups with biochar added are not differed greatly, being 7.22 and 7.24, respectively, while those of the T1 and T3 groups are 7.53 and 7.33, respectively. The significant increase in pH of the fermentation broth caused by the addition of carbonyl iron may be caused by the oxygen-absorbing corrosive effect of iron induced by the addition of carbonyl iron in a partial-neutral environment. The pH of the T1 and T3 groups decreases more sharply than that of the T1 and CK groups as acidification proceeds, with the largest decrease in the T1 group, and the trends in the T2 and CK groups remain consistent. T1 group also shows the earliest pH rebound, with a trend of increase after the $5^{th}$ d, while the rebound in T3 and CK groups starts from the $10^{th}$ d. T2 group shows the latest pH rebound, which starts from the $15^{th}$ d. As fermentation progresses to the 20th d, the pH values of both T1 and T3 groups are increased to the same level as that of the CK group, and remain on a steady rise thereafter; there is a slight fluctuation in the CK group from 45d-60d, with pH dropping to 8.06 and then recovering to 8.21; in group T2, the pH value is always lower than other treatments, but it is maintained within the suitable range. The pH values of T1, T2, T3 and CK groups at the end of fermentation are 8.43, 8.28, 8.42, 8.39, respectively, such results show that the biochar may lower the pH of the fermentation broth, the carbonyl iron may increase the pH of the fermentation broth, and the coupled addition of biochar and carbonyl iron has a more significant effect on the improvement of the pH.

Figure 4:
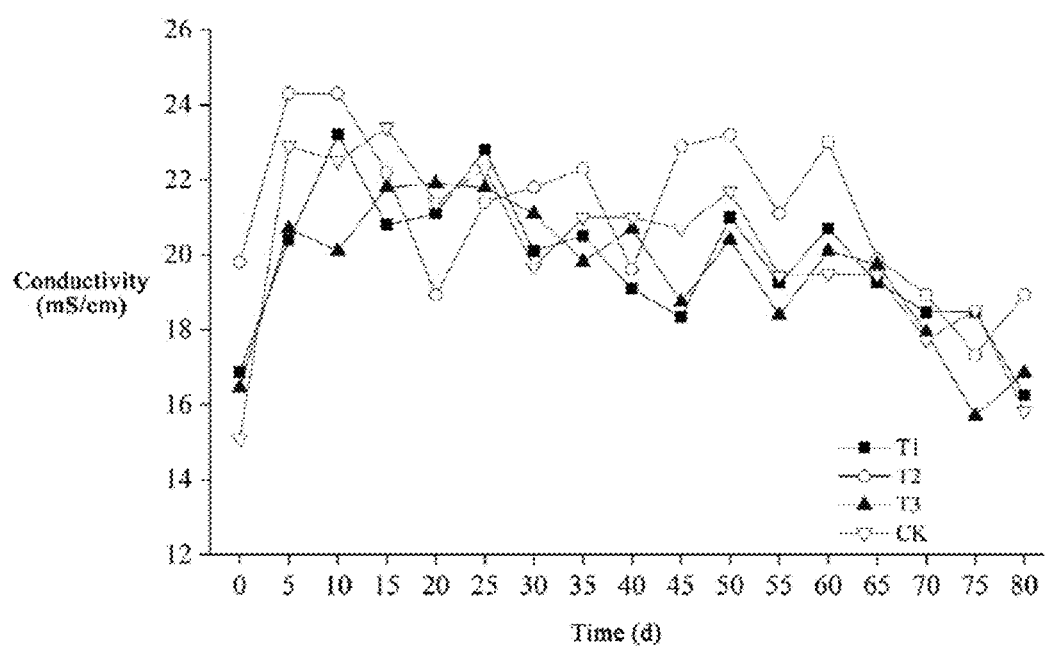
FIG. 4 shows the conductivity variation of the fermentation broth of the anaerobic digestion.

The conductivity of the anaerobic digestion broth is in a positive correlation with the concentration of soluble salts, where a too high or too low concentration of soluble salts will adversely affect the activity of the anaerobic digestive microorganisms. As observed from FIG. 4, the conductivity of all treatments, although showing fluctuations, is generally in a trend of first increasing and then decreasing. In the first 5 d of fermentation, the concentration of soluble salts in the broth is increased as a result of the hydrolysis of large molecules of insoluble organic matter into the dissolved state, and the EC value rises accordingly. At the start of fermentation, the conductivities of T1, T2, T3 and CK groups are 16.87 millisiemens per centimeter (mS/cm), 19.80 mS/cm, 16.46 mS/cm, and 15.08 mS/cm, respectively. The biochar and carbonyl iron, either added individually or coupled, may increase the conductivity of the fermentation broth at startup, and the boosting effect on the broth is more significant with the addition of biochar alone, potentially a result of the release of cations from the biochar into the fermentation broth. Across the fermentation cycle, the average conductivities of the T1, T2, T3 and CK groups are 19.80 mS/cm, 21.17 mS/cm, 19.54 mS/cm and 20.12 mS/cm, respectively. Generally speaking, the conductivity of the fermentation broth is reduced by the addition of carbonyl iron.

Comparative Embodiment 1

The procedure of T1 reactor is the same as that in Embodiment 1, and the only difference is that carbonyl iron is replaced by nano zero-valent iron.

The cumulative methane production of this comparative embodiment is 243 mL/g VS.

Comparative Embodiment 2

The procedure of T1 reactor is the same as that in Embodiment 1, except that carbonyl iron is replaced by nano zero-valent iron, and 2 g/L of glycerol trioleate is added to the reaction broth.

The cumulative methane production of this comparative embodiment is 292 mL/g VS.

The above-mentioned embodiments only describe the preferred mode of the present disclosure, and do not limit the scope of the disclosure. Under the premise of not departing from the design spirit of the disclosure, various modifications and improvements made by ordinary technicians in the field to the technical scheme of the disclosure shall fall within the protection scope determined by the claims of the disclosure.

What is claimed is:

1. A method for promoting anaerobic digestion using carbonyl iron, wherein the method comprises: adding carbonyl iron into a fermentation broth for anaerobic digestion; and
   a substrate added in the fermentation broth is animal manure, kitchen waste or tail vegetables.

2. The method for promoting anaerobic digestion using carbonyl iron according to claim 1, wherein an addition amount of the carbonyl iron is 6 wt % of volatile solids of the substrate.

3. The method for promoting anaerobic digestion using carbonyl iron according to claim 1, wherein an addition amount of a biochar is 2 wt % of the volatile solids of the substrate.

* * * * *